United States Patent [19]

Ingal et al.

[11] Patent Number: 5,579,363
[45] Date of Patent: Nov. 26, 1996

[54] METHOD FOR OBTAINING THE IMAGE OF THE INTERNAL STRUCTURE OF AN OBJECT

[75] Inventors: Viktor N. Ingal; Elena A. Belyaevskaya, both of Sankt-Peterburg; Valery P. Efanov, Moscow, all of Russian Federation

[73] Assignee: V-Ray Imaging Corporation

[21] Appl. No.: 500,559

[22] Filed: Jul. 11, 1995

Related U.S. Application Data

[63] Continuation of Ser. No. 229,887, Apr. 19, 1994, abandoned, which is a continuation of Ser. No. 956,880, Dec. 11, 1992, Pat. No. 5,319,694.

[30] Foreign Application Priority Data

May 14, 1991 [RU] Russian Federation ............... 4934958

[51] Int. Cl.$^6$ ..................................................... G21K 1/06
[52] U.S. Cl. ................................. 378/84; 378/85; 378/82
[58] Field of Search ............................. 378/84, 85, 83, 378/82

[56] References Cited

U.S. PATENT DOCUMENTS 5,319,694  6/1994  Ingal et al. ................................ 378/84

FOREIGN PATENT DOCUMENTS 1402871  6/1988  Russian Federation .
2137453  10/1984  United Kingdom .
2203620  10/1988  United Kingdom .

*Primary Examiner*—Craig E. Church
*Attorney, Agent, or Firm*—Paul D. Grossman

[57] ABSTRACT

This invention relates to nondestructive testing of the internal structure of objects.

The method for obtaining the image of The internal structure of an object consists in that the flux of a penetrating radiation emitted by a source (1) is collimated by a single-crystal monochromator (4), an object (7) is irradiated with the thus-collimated radiation, the radiation transmitted through the object (7) is collimated by a single-crystal (8) and then registered by a detector (9). According to the invention, use is made for irradiating the object, of an asymmetrical reflection of the radiation from the single-crystal monochromator (4), a pseudosheet-like beam (5) is formed, having a wide wavefront and a divergence in the Bragg diffraction plane at least twice as little as the width of the Bragg reflection of the single-crystal (8), which is set in the position of Bragg reflection with respect to the pseudosheet-like beam (5) formed by the single-crystal monochromator (4).

The method is aimed preferably for diagnosing polymer and ceramic products, as well as for medical diagnosis.

17 Claims, 3 Drawing Sheets

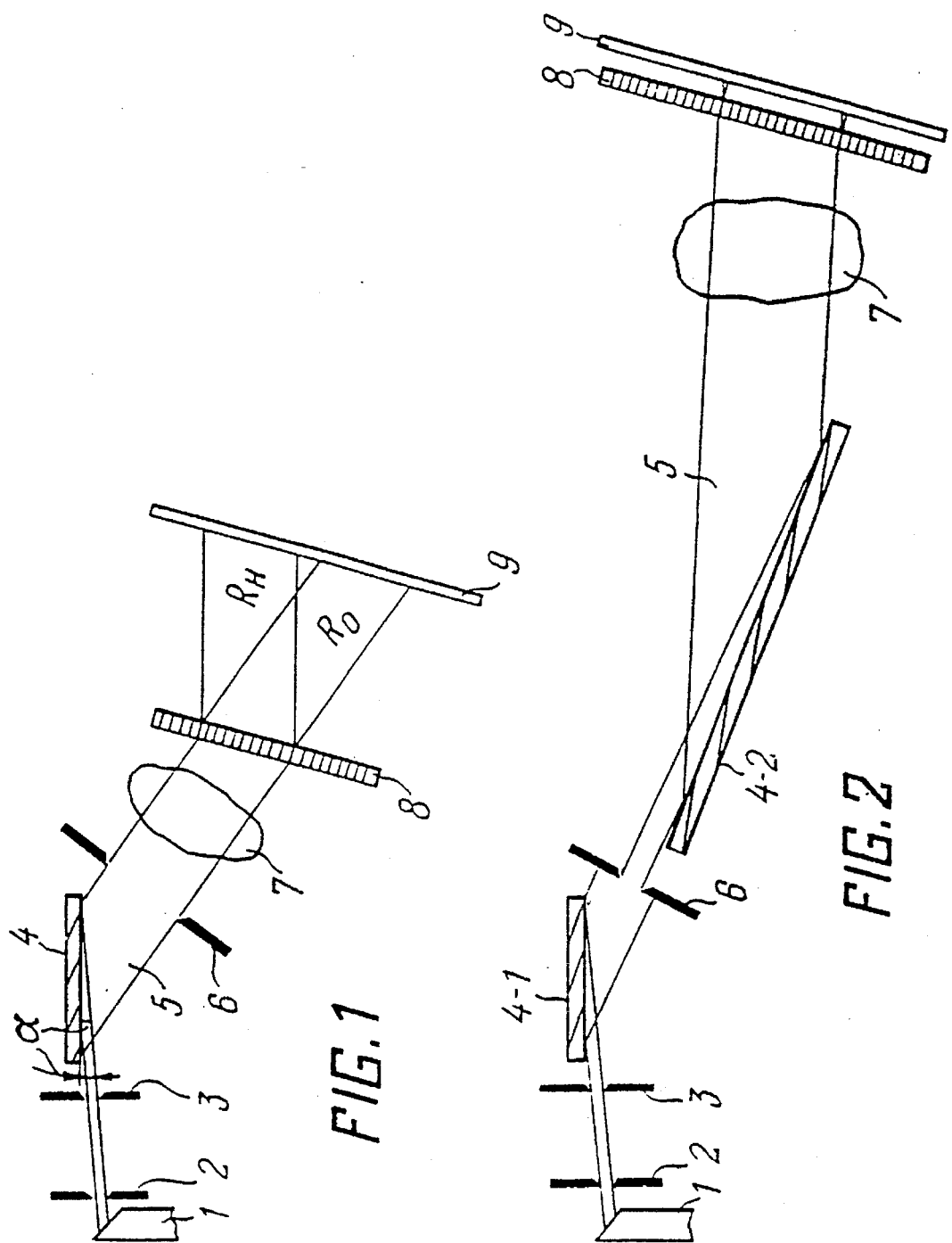

1

METHOD FOR OBTAINING THE IMAGE OF THE INTERNAL STRUCTURE OF AN OBJECT

This application is a continuation of application Ser. No. 08/229,887, filed Apr. 19, 1994 now abandoned, which is a continuation of application Ser. No. 07/956,880, filed Dec. 11, 1992 (which is now U.S. Pat. No. 5,319,694).

TECHNICAL FIELD

This invention relates generally to methods for non-destructive testing of objects using penetrating radiation and has particular reference to methods for obtaining the image of the internal structure of an object.

BACKGROUND ART

One state-of-the-art method for obtaining the image of the internal structure of an object is widely known to comprise irradiation of the object under test with an X-ray beam and recording the radiation that has passed through the object with the aid of a detector, e.g., an X-ray sensitive film. Useful information appears, after decoding X-ray photographs, as data on the amount of radiation absorbed by the areas of the object under test having different degrees of radiotranslucency.

However, X-rays used in the heretofore-known method is a continuous X-ray spectrum polychromatic radiation. This offers some difficulties in interpretation of the results obtained, inasmuch as the long-wave spectal components are as a rule absorbed by the object itself and the proportion of absorbed radiation varies from one object to another, which cannot be allowed for at all times. This in turn results in adversed reliability of the results of inspection of an internal structure of the object under test.

One mope state-of-the-apt method for obtaining the image of the internal structure of an object is known to provide irradiation of the object under test with an X-ray beam collimated by a single-crystal monochromator, followed by recording the radiation passed through the object in a detector (W. A. Ellingson, M. W. Vanier "Application of Dual-energy X-ray Computed Tomography to Structural Ceramics", Adv., X-ray, Anal., 1988, v.32, pp.629–640).

The method mentioned above provides for higher sensitivity and reliability of the results of inspection due to the use of monochromatic radiation.

However, the method in questions is practically unsuitable, as the one discussed before, for testing the internal structure of objects featuring weak absorption of a penetrating radiation, especially such portions of the object under test, wherein the degree of X-ray transparency is close to that of the surrounding medium.

Finally, a method for obtaining the image of the internal structure of an object is also known, consisting in that the flux of a penetrating radiation emitted by a source is collimated by a first single-crystal monochromator, the object is irradiated with the collimated radiation, the radiation that has passed through the object is collimated by a second single-crystal and is then recorded by a detector (SU, A, 1,402,871).

According to the method under discussion, the radiation incident upon the object and passed therethrough is effected in an angular range corresponding to the characteristic angles of refraction of the radiation in question effective at the boundary of different-density media of the object under test. Used for collimation are perfect-quality single crystals placed in front of and past the object under test parallel to each other so that the Miller indexes of the reflecting surfaces thereof have the same value and be opposite as to sign.

With the above condition fulfilled the rays that have not refracted when passing through the object and did not deflected from the initial direction set by the first single-crystal monochromator, are Deflected from the second single-crystal which is recorded by the detector in a diffracted beam. At the same time the rays that have deflected from the initial direction at the boundary of two different-density media go beyond the limits of the range of Bragg reflection of the second single crystal so that a drop of the radiation intensity in the detector of the diffracted beam at said interface. Thus, the image of the internal structure of an object is established according to the method discussed above. The method is featured by a higher sensitivity compared with the aforediscussed methods for testing the internal structure of an object against the amount of absorbed radiation and is capable of testing such objects that are characterized by weak absorption of penetrating radiation.

However, when the object under test features an a boundary between two media, wherein their refractive indices are so close to each other that the angle of deflection of rays at said boundary falls within the range of the angles of Bragg reflection of the second single crystal, such a boundary would not be registered by the detector because the rays deflected at said boundary get onto the detector receiving surface simultaneously with the pays that have been passed through the object without deflection. Thus, the deflected rays do not cause a perceptible reduction of the radiation intensity against the background of the non-deflected pays.

SUMMARY OF THE INVENTION

The present invention is aimed at the provision of a method for obtaining the image of the internal structure of an object, which would make it possible to register on the detector the rays that have deflected at the boundary of two media in the object under test for angles smaller than those in the range of Bragg reflection in the second single crystal, thereby increasing the sensitivity and hence making the method more informative.

The aforesaid aim is attained due to the fact that in a method for obtaining the image of the internal structure of an object, consisting in that the flux of a penetrating radiation emitted by a source is collimated by a first single-crystal monochromator, the object under test is irradiated with said collimated radiation, the radiation that has passed through said object is collimated by a second single crystal monochromator and is registered by a detector, according to the invention, the object under test is irradiated with asymmetrical reflection of radiation from a single-crystal monochromator and a wide-wavefront pseudosheet-like beam is formed, featuring its divergence in the Bragg diffraction plane at least twice as little as The width of the Bragg reflection range of the second single-crystal, while said second single-crystal is set in a position at which the condition of Bragg reflection with respect to the pseudosheet-like beam formed by the single-crystal monochromator is fulfilled for the reflecting surfaces of said second single-crystal.

It is expedient that for obtaining the maximum image contrast the second single-crystal be rotated, prior to registration, round an axis lying in its plane and being square with the Bragg diffraction plane within the range of Bragg reflection angles, the interference patterns of the internal structure Of the object under test be observed at various angles of rotation of the single-crystal and be recorded with the latter single-crystal in a position corresponding to a maximum contrast of the image of the desired area of the object under test.

To enhance the image contrast it is practicable to deflect the second single-crystal from its exact exact Bragg position in both directions alternatively for equal angles relative to the Bragg position in the range of the Bragg diffraction angles, to obtain the images of the object in both of said positions, to perform an algebraic addition of said images, and To record the result of said addition.

It is possible to observe the image of the internal structure of the object in the transmitted and diffracted radiation beams at a Time and To record the image which has a higher intensity, thereby a possibility of detecting artifacts in the image is provided.

Whenever The thickness of the second single-crystal is such that less than 10 percent of the penetrating radiation is absorbed therein, The image contrast can be enhanced by performing algebraic addition of the images obtained in the transmitted and diffracted beams and recording the result of said addition.

To eliminate the elements resulting from photoelectric absorption of the radiation by the object under test, the second single crystal is first to be deflected for an angle exceeding the range of Bragg reflection angles, whereupon the image of the object obtained with the single-crystal in said deflected position is to be algebraically added to the image observed at the point of maximum contrast and the result of addition is to be recorded.

When using a source of hard radiation having a wavelength below 0.3 A, it is expedient, with the purpose of reducing the overall dimensions of the device, that the image be recorded immediately past the output face of the second single-crystal.

The method for obtaining the image of the internal structure of an object according to the invention is featured by a high sensitivity to low density gradients and is instrumental in obtaining contrast images of internal structure of objects which also carry information on the object interfaces at which the rays of a penetrating radiation have been deflected for angles smaller than the range of Bragg reflection angles of the second single-crystal.

The method, according to the invention, yields essentially best results with zero photoelectric absorption in the material of the object under test. Practical application of the method provides, with a minimum absorbed radiation dose, its high sensitivity and information-bearing capacity which renders the method most promising for use in medicine.

BRIEF DESCRIPTION OF THE DRAWINGS

In what follows the present invention will now be disclosed in a detailed description of some specific illustrative embodiments thereof with reference to the accompanying drawings, wherein:

FIG. 1 is a schematic view of a device for carrying into effect the method for obtaining the image of internal structure of The object under test, according to the invention;

FIG. 2 is a view of FIG. 1 showing an embodiment of the device for use of a hard radiation;

BEST MODES FOR CARRYING OUT THE INVENTION

Figure 3:
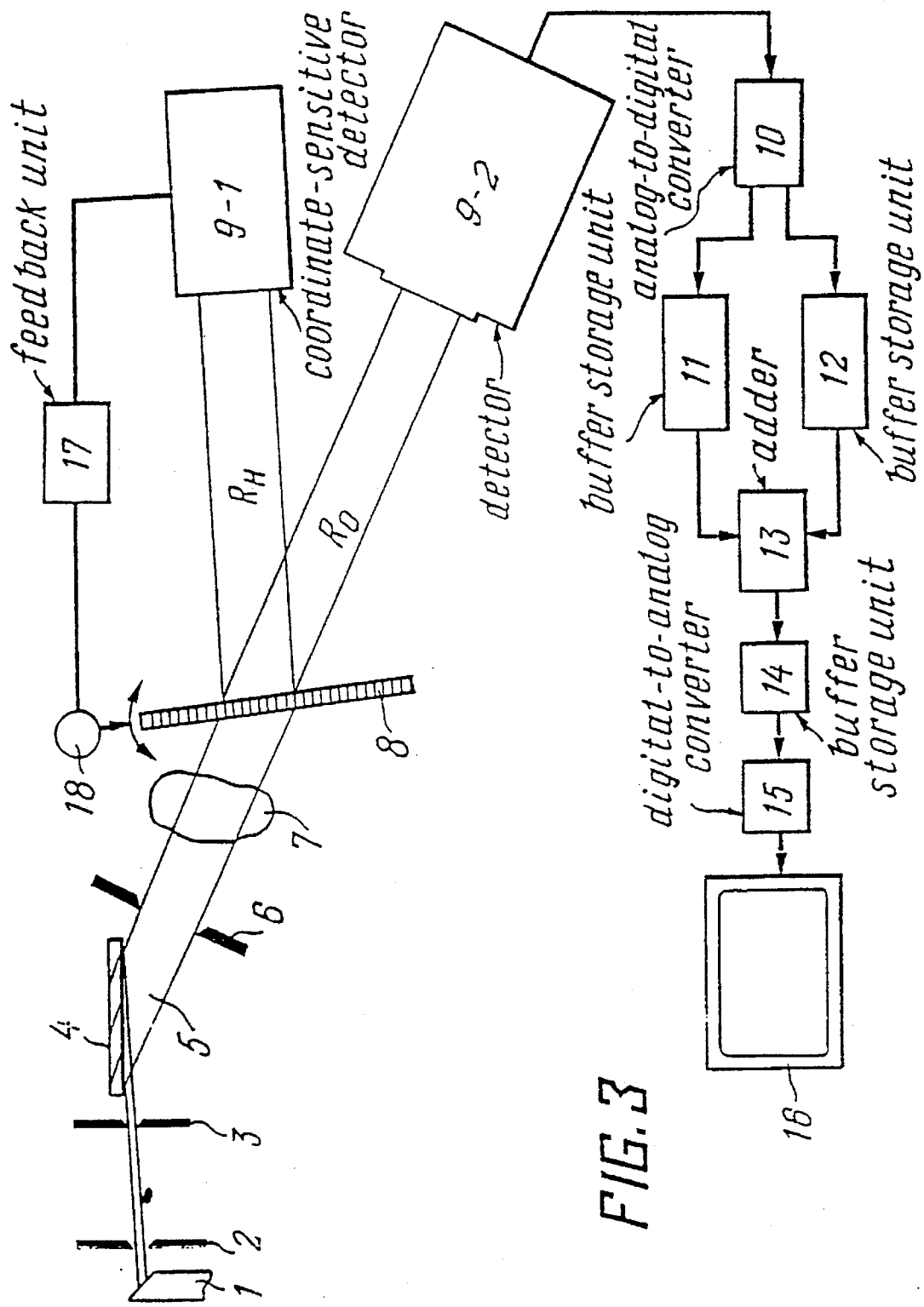
FIG. 3 is a view of FIG. 1 showing a structural diagram of the unit for algebraic addition of images.

The device for carrying into effect the method for obtaining the image of an internal structure of the image under test, according to the invention, as schematically shown in FIG. 1 comprises a source 1 of a penetrating radiation, e.g., X-Fays, slit arrangements 2, 3 forming the beam of the radiation source 1, a single-crystal monochromator 4 placed across the pathway of said radiation beam and so oriented that the radiation emitted by the source 1 is incident upon the input face of the single-crystal monochromator at a grazing angle α. An object 7 under test is placed across the pathway of a beam 5 reflected from the single-crystal monochromator 4 past a slit arrangement 6, said object 7 being set in holders (omitted in the Drawing). Arranged past the object 7 as along the path of radiation is a second single-crystal 8 hereinafter referred to as the crystal-analyzer 8, and a coordinate-sensitive beam detector 9.

According to an embodiment of the device presented in FIG. 2, as distinct from the device illustrated in FIG. 1, the single-crystal monochromator 4 is built up of two single crystals 4-1 and 4-2.

The method for obtaining the image of internal structure of an object, according to the invention, is carried into effect as follows.

A flux of X-rays emitted by the source 1, e.g., an X-ray tube with a Mo anode, is collimated by the single-crystal monochromator 4, using an asymmetric reflection of the radiation from a system of planes (hkl), e.g., (220) of the single-crystal monochromator 4, and a pseudo-sheet-like beam 5 is shaped, having a broad wavefront and a divergence in the Bragg diffraction plane at least twice as little as the width of the Bragg reflection range of the single-crystal 8.

Used as the single-crystal monochromator 4 is a perfect crystal, such as that of silicon, germanium, or quartz, having an area of its effective surface measuring tens or hundreds of square centimeters and a factor of asymmetry in excess of four. In this particular case there is selected such a single-crystal monochromator that has a factor of asymmetry equal to 25. This means, first, that the front of an original beam incident upon the input plane of the single-crystal monochromator 4 will be enlarged by a factor of 25 in the reflected beam 5 and, secondly, that the divergence of the reflected beam 5 will be less than the width of the angular range of Bragg reflection by a factor of $\sqrt{25}$.

The smaller the grazing angle α of a beam incident upon the single-crystal monochromator 4 the higher the degree of asymmetry of the radiation used and hence the lower the divergence of the pseudosheet-like beam 5 shaped by said single-crystal monochromator 4. The angle α of beam grazing is selected in the limits of $Q_B \geq \alpha > \alpha_c$, where $\alpha_c$ is the angle of total external reflection of X-rays from the single-crystal monochromator 4. Concurrently with a reduction of the angular width of X-ray beam incident upon the single-crystal monochromator 4 and formation of a pseudosheet-like wave, the front of said wave is extended. When the degree of reduction of said angular width or the degree of increase of said wavefront is not sufficient for shaping the beam 5 irradiating the object 7 use is made of a black (consisting two or more) of the single-crystal monochromators 4-1, 4-2 as shown in FIG. 2. For instance, when the factor of asymmetry of the single-crystal monochromator 4-1 equals 25 and that of the single-crystal monochromator 4-2 is 30, so the beam 5 will feature a divergence of 0.08".

Under the aforedescribed conditions one or more single-crystal monochromators q are to shape the pseudosheet-like beam 5 having characteristics adequate for establishing an interferogram (grating) image of the object 7 irradiated by said beam 5.

The crystal-analyzer 8 is to be so positioned as to fulfill Bragg reflection conditions, for its reflecting planes, with respect to the pseudosheet-like beam 5 shaped by the single-crystal monochromator 4, e.g., the crystal-analyzer 8 is placed in reflection (220).

Used as the crystal-analyzer 8 is a perfect crystal free from any macrostresses, dislocations, or second-phase inclusions and having its degree of perfectness high enough not to introduce its own distortions in the image of the object 7.

The crystal analyzer 8 can be set in a position, wherein its reflecting planes are oriented "for transmission" or "for reflection". The reflecting planes themselves may be both symmetrical and asymmetrical.

The rays incident upon the input face of the crystal-analyzer 8 and belonging to the pseudosheet-like beam 5 shaped by the single-crystal monochromator 4 that have been passed through the object 7 without deflection, and the rays that have undergone microscattering at the boundary of different-density media and imparted an additional phase shift, interfere with the reflecting planes of the crystal-analyzer 8. Thus, participating in the formation of an interference image of the object 7 are both the rays that have passed through the object 7 without deflection and the rays that have deflected at the boundary, including those deflected for angles smaller than the angles of collimation performed by the single-crystal monochromator 4 and by the crystal-analyzer 8 situated past the object 7. As a result, an interference image of the internal structure of the object 7 is produced at the output of the crystal-analyzer 8. The interference image thus obtained displays not only the boundaries resulting from a lower radiation intensity (shown on a positive as black areas against a lighter background) due to deflection of the rays at the boundary of the media in the object for angles exceeding the range of the Bragg reflection angles but also bears an information on the boundaries at which the rays have deflected for angles smaller than those of the Bragg reflection range for the crystal-analyzer 8. These boundaries are present in the image of the object 7 as additional black-and-white and white-and-black contrast images.

According to method of the invention, an angular position of the crystal-analyzer 8 is changed, prior to registering the internal structure of the object 7 using the coordinate-sensitive detector 9 transmitting the image to the monitor screen, by rotating said crystal-analyzer about an axis situated in its plane and arranged square to the Bragg diffraction plane, both clockwise and counterclockwise relative the exact Bragg position $Q_B$ in the range of the Bragg reflection angles, otherwise speaking within the width of the reflection curve. In this case the image of the boundaries of interfaces in the object which are featured by different density gradients, is observed at a maximum contrast only when the crystal-analyzer 8 assumes a position most suitable for each of said boundaries. Thus, for instance, the angular position of the crystal-analyzer 8 corresponding to the point A in FIG. 4 will be better represent an external contour of the object, whereas its angular position corresponding to the point C will represent an internal structure of the object. An exact Bragg position $Q_B$ of the crystal-analyzer 8 (FIG. 1) practically never corresponds to a maximum contrast of the image of the contours of the object and of its internal structure. By deflecting the crystal-analyzer 8 one is to watch the interferogram images of the internal structure of the object 7 and to select such a position of the crystal-analyzer 8 that gives the image of the parts involved has a maximum contrast.

Figure 4:
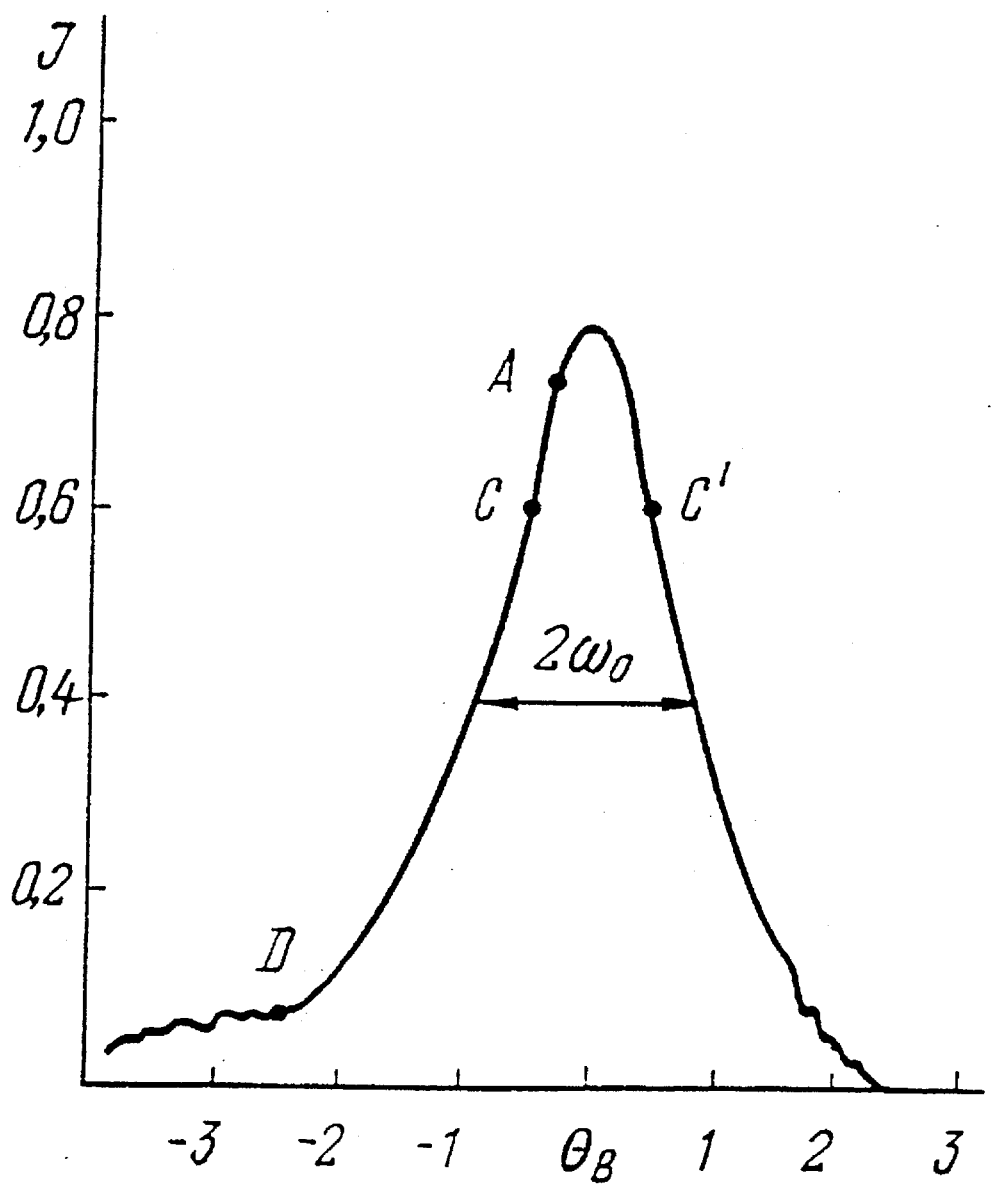
FIG. 4 presents a distribution curve of integral intensity J of a beam reflected from the second single-crystal (reflection curve), wherein plotted as abscissa is the angular deflection $Q_B$ of the second single-crystal from an exact Bragg position expressed in terms of units of half-width $W_o$ of the distribution curve.

According to an alternative embodiment of the method, according to the invention, the crystal-analyzer 8 is deflected for equal angles clockwise and counterclockwise with respect to an exact Bragg position $Q_B$ in the range of Bragg reflection angles (points C and C' in FIG. 4). The images obtained with the crystal-analyzer 8 in the first and second positions are added algebraically (with opposite signs) and the result of addition is recorded. Such an algebraic addition of similar images differing only in the sign of contrast (that is, one black-and-white and the other white-and-black) makes it possible to substantially enhance the contrast of the image obtained and as a result of such addition.

According to the method of the invention, both of object 7, that is, the transmitted beam $R_o$ and the diffracted beam $R_H$. Thus, simultaneous-observation of the object in both of the beams $R_o$ and $R_H$ enables one to detect artifacts in the image, such as e.g., defects of the recorder or detector. The point is that the image contrast of the same boundary between two media in the object 7 as seen in the beams $R_o$ and $R_H$ is different for each beam but is obligatorily present in both beams. When the image detected in one of such beams has some elements absent in the image registered in the other beam, this is indicative of the presence of an incidental defect, e.g., that of the emulsion on an X-ray film.

When the thickness of the crystal-analyzer 8 is such that less than 10 percent of the penetrating radiation is absorbed therein, the contrast of the image of the boundaries in the object as seen in the transmitted beam $R_o$ and in the diffracted beam $R_H$ is as a rule complementary, that is, black-and-white and white-and-black. In this case the images registered in the beams $R_o$ and $R_H$ are added together with the opposite signs. The contrast of the images of the boundaries in the resultant image is enhanced additionally due to subtraction of information on the areas wherein only photoelectric absorption occurs.

The aforesaid embodiment of the method is instrumental in attaining a higher image contrast without precision displacement of the crystal-analyzer 8.

One more embodiment of the method disclosed-herein consists in that the crystal-analyzer 8 is first deflected for an angle exceeding the range of Bragg reflection angles (point D in FIG. 4) to obtain the image of the object 7 with the aforesaid position of the crystal-analyzer 8. The image contains information only on the distribution in the object 7 of areas differing in photoelectric absorption. Once said image has been detected, the crystal-analyzer 8 is set to the position at which the maximum contrast of the object image is attained (e.g., point A in FIG. 4) and the images having opposite signs are added together, after which the image gets rid of the contrast resulting from photoelectric absorption.

When using a hard radiation source featuring its wavelength below 0.3Å which is the case with medical examination of a living organism, the Bragg angles of reflecting planes are equal to several degrees so that the detector 9 must be spaced a considerable distance (about 1 m) from the crystal-analyzer 8 in case the crystal-analyzer 8 is oriented "for transmission" for separate registration of the images of the object 7 in the transmitted beam $R_o$ and diffracted beam $R_H$, with the resultant considerable increasing of the overall dimensions of the device.

In such a case the image of the object 7 is detected immediately past the output plane of the crystal-analyzer 8 in a zone where the transmitted and diffracted beams $R_o$, $R_H$, respectively has not yet been practically separated from each other. This makes it possible to obtain contrast images with the same overall dimensions of the device. To this aim the detector 9 is to be situated close to the output plane of the crystal-analyzer 8 as seen in FIG. 2.

FIG. 3 represents one of possible variants of a block-diagram of a device for effecting numerical algebraical addition of images. In addition to the elements described with reference to FIG. 1, the device of FIG. 3 comprises two coordinate-sensitive detectors 9-1, 9-2 of which the detector 9-1 is adapted for detecting the diffracted beam $R_H$ and the detector 9-2, for detecting the transmitted beam $R_o$. Connected to the output of the detector 9-2 is an analog-to-digital converter 10 to the outputs of which are buffer storage units 11, 12 which in turn are connected, through their outputs, to the inputs of an adder 13. Connected to the output of the adder 13 are series-connected a buffer storage unit 14, a digital-to-analog converter 15, and a video monitor 16. The output of the detector 9-1 is connected, via a feedback unit 17, to the input of the precision displacement actuator of the crystal-analyzer 8.

Each of the pairs of detected images subject to addition is converted by the analog-to-digit converter 10 into a sequence of numerical codes carrying information on the signal amplitude in each of the image elements. The coordinates of the images elements are defined by the position of a code corresponding to a given element in the numerical sequence. The adder 13 carries out an algebraic element-by-element addition of the codes, and the resultant information is put down in the buffer storage unit 14 using likewise the element-by-element technique, whence the information is processed in the digit-to-analog converter 15 and then delivered to the screen of the video monitor 16.

The method, according to the invention, is suitable for testing objects having an amorphous structure, a crystalline structure, or a composition structure of both. The objects under test can also be of biological origin.

The sole limitation placed upon the object under test consists in that a maximum absorption of a penetrating radiation therein must not exceed 50 percent, otherwise the beam that have undergone microscattering at the interfaces in the object will be absorbed therein so that no interferogram images will be observed.

Thus, use of a pseudosheet-like beam formed by reflection from asymmetric planes of a single-crystal monochromator, for irradiation of the object under examination results in an increased size of the area under examination and in a higher sensitivity of the method to low density gradients, inasmuch as, according to the invention, accuracy of selection of an angular deflection of the detected beams and of its determination is defined not by the width of the reflection curve which is the case with the known method but by the divergence of the pseudosheet-like beam incident upon the object under test, which divergence can be substantially smaller than said width of the reflection curve. It is due to the aforesaid feature that the contrast at the boundaries of the media having close values of the refractive index of the radiation used is also increased.

A possibility of obtaining a number of images with the crystal-analyzer 8 in different angular positions enables one to get a more detailed knowledge of the internal structure of the object, since the beams that have deflected for different angles at the boundaries are formed in each angular position of the crystal-analyzer 8.

Simultaneous registering of images in two beams, the transmitted and diffracted ones, enables one to define more exactly the reliability of minor and low-contrast image elements and to eliminate errors in interpretation of the image due to imperfection of the image detector. In addition, algebraic addition of said images enhances the contrast of the boundaries between the different-density media, which is due to elimination of a background resulting from photoelectric absorption of radiation in the object, and by virtue of additional distinction of the boundaries.

The same aim is attained by consecutive registration of images with the crystal-analyzer assuming such angular positions that are deflected for equal angles from exact Bragg position, followed by algebraic addition of said images, and also by consecutive registration of said images with the crystal-analyzer 8 assuming two angular positions, one of which falls within the limits of the reflection curve and the other is outside the limits of that curve.

Registration of a combined image resulting from superposition of images formed in the transmitted and diffracted beams simplifies substantially the image formation process involving the contrasting of the boundaries in the internal structure of the object under test, using a hard radiation with small diffraction angles and inconsiderable resolution loss.

The method disclosed herein will find most utility when using powerful radiation sources, in particular, highly penetrating radiation sources, and is applicable for examination of-biological objects, ceramics, composite materials, polymer ones inclusive, as well as mixtures of different-density liquids.

INDUSTRIAL APPLICABILITY

The present method for obtaining the image of the internal structure of an object can find application for nondestructive testing of objects made of a variety of materials, including metals, ceramics, composition materials, polymers, and biological objects.

The method is preferably applicable for diagnosis of objects featuring a low degree of absorption of a penetrating radiation and having low gradients of density of its components, e.g., for diagnosing living organisms, or polymer and ceramic products.

We claim:

1. An apparatus for obtaining an image of the internal structure of an object adapted for use with a penetrating radiation, the apparatus comprising:

a source of penetrating radiation;

a crystal monochrometer having a reflection plane for forming a plane beam of the penetrating radiation, the crystal monochrometer being located upstream from such object;

a crystal analyzer including a reflection plane and a Bragg reflection range for forming an interference image of such object, the crystal analyzer being located downstream from such object, the crystal analyzer being positioned to effect the Bragg reflection of such plane beam, and the crystal analyzer having a Bragg reflection range which is at least twice the divergence of such plane beam; and a coordinate-sensitive beam detector positioned to detect the penetrating radiation which is Bragg reflected by the crystal analyzer.

2. The apparatus of claim 1 wherein the crystal monochrometer is a block of single-crystal monochrometers.

3. The apparatus of claim 1 further including a first slit located upstream from the crystal monochrometer for forming a defined beam of such penetrating radiation.

4. The apparatus of claim 1 further including a second slit located downstream from the crystal monochrometer and upstream from such object for further forming the beam of penetrating radiation.

5. The apparatus of claim 1 wherein the thickness of the crystal analyzer is such that less than ten (10) percent of such penetrating radiation incident on the crystal analyzer is absorbed therein.

6. The apparatus of claim 1 further including a precision displacement actuator for varying the position of the crystal analyzer.

7. The apparatus of claim 1 wherein the coordinate-sensitive beam detector is X-ray-sensitive film.

8. The apparatus of claim 1 wherein the coordinate-sensitive beam detector is located immediately downstream from an output plane of the crystal analyzer such that an image of the object in such transmitted penetrating radiation and an image of the object in such diffracted penetrating radiation are not separately registered by the coordinate-sensitive beam detector.

9. The apparatus of claim 1 wherein the coordinate-sensitive beam detector is located sufficiently downstream from the crystal analyzer such that an image of the object in such transmitted penetrating radiation and an image or the object in such diffracted penetrating radiation are separately registered by the coordinate-sensitive beam detector.

10. The apparatus of claim 1 further including a holder for holding such object such that such plane beam is incident upon such object.

11. The apparatus of claim 1 wherein the coordinate-sensitive beam detector comprises:

a first coordinate-sensitive beam detector located to detect such penetrating radiation which is transmitted by the crystal-analyzer;

a second coordinate-sensitive beam detector located to detect such penetrating radiation which is diffracted by the crystal analyzer;

a precision displacement actuator for varying the position of the crystal analyzer, the actuator being controllably connected to an output of the first coordinate-sensitive detector;

a first buffer storage unit connected to an output of the second coordinate-sensitive beam detector for storing the output of the second coordinate-sensitive beam detector at a first time;

a second buffer storage unit connected to the output of the second coordinate-sensitive beam detector for storing the output of the second coordinate-sensitive beam detector at a second time; and an adder for adding the contents of the first buffer storage unit and the contents of the second buffer storage unit.

12. The apparatus of claim 11 further comprising a video monitor connected to an output of the adder for display of the output of the adder.

13. The apparatus of claim 1 wherein the penetrating radiation is hard radiation having a wavelength below 0.3 Å.

14. The apparatus of claim 13 wherein the penetrating radiation is X-ray radiation.

15. The apparatus of claim 1 wherein the reflection plane of the crystal monochrometer is asymmetric.

16. The apparatus of claim 15 wherein the reflection plane of the crystal monochrometer has a factor of asymmetry in excess of four.

17. The apparatus of claim 16 wherein the reflection plane of the crystal monochrometer has a factor of asymmetry of approximately 25.

* * * * *